US00PP12991P2

(12) United States Plant Patent
Noodelijk

(10) Patent No.: US PP12,991 P2
(45) Date of Patent: Sep. 24, 2002

(54) CHRYSANTHEMUM PLANT NAMED 'VIRUNGA YELLOW'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/561,933

(22) Filed: May 1, 2000

(51) Int. Cl.[7] ..... A01H 5/00
(52) U.S. Cl. ..... Plt./295
(58) Field of Search ..... Plt./295

*Primary Examiner*—Bruce R. Campell
*Assistant Examiner*—Annette H. Para
(74) *Attorney, Agent, or Firm*—Parkhurst & Wendel, L.L.P

(57) ABSTRACT

A Chrysanthemum plant named 'VIRUNGA YELLOW' characterized by its LARGE sized blooms with YELLOW ray-florets and YELLOW-GREEN disc florets.

2 Drawing Sheets

RELATED CULTIVARS

'VIRUNGA YELLOW' is related to VIRUNGA (copending U.S. application Ser. No. 09/561,939). 'VIRUNGA YELLOW' is a color mutant of VIRUNGA.

BACKGROUND OF THE INVENTION

'VIRUNGA YELLOW' is a product of a breeding and selection program which had the objective of finding color mutants of VIRUNGA. The new plant of the present invention comprises a new and distinct cultivar of chrysanthemum plant that is a natural occuring sport of a parent chrysanthemum named VIRUNGA. A comparison with Parent chrysanthemum VIRUNGA is also made in this application. The new cultivar was discovered as a whole plant mutation in September 1998 by Rob Noodelijk in a controlled environment (greenhouse) in Rijsenhout Holland. The first act of asexual reproduction of 'VIRUNGA YELLOW' was accomplished when vegetative cuttings were taken from the initial selection in November 1998 in Rijsenhout Holland.

SUMMARY OF THE INVENTION

The present invention is a new and distinct variety of chrysanthemum bearing large sized blooms with yellow ray-florets and yellow-green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
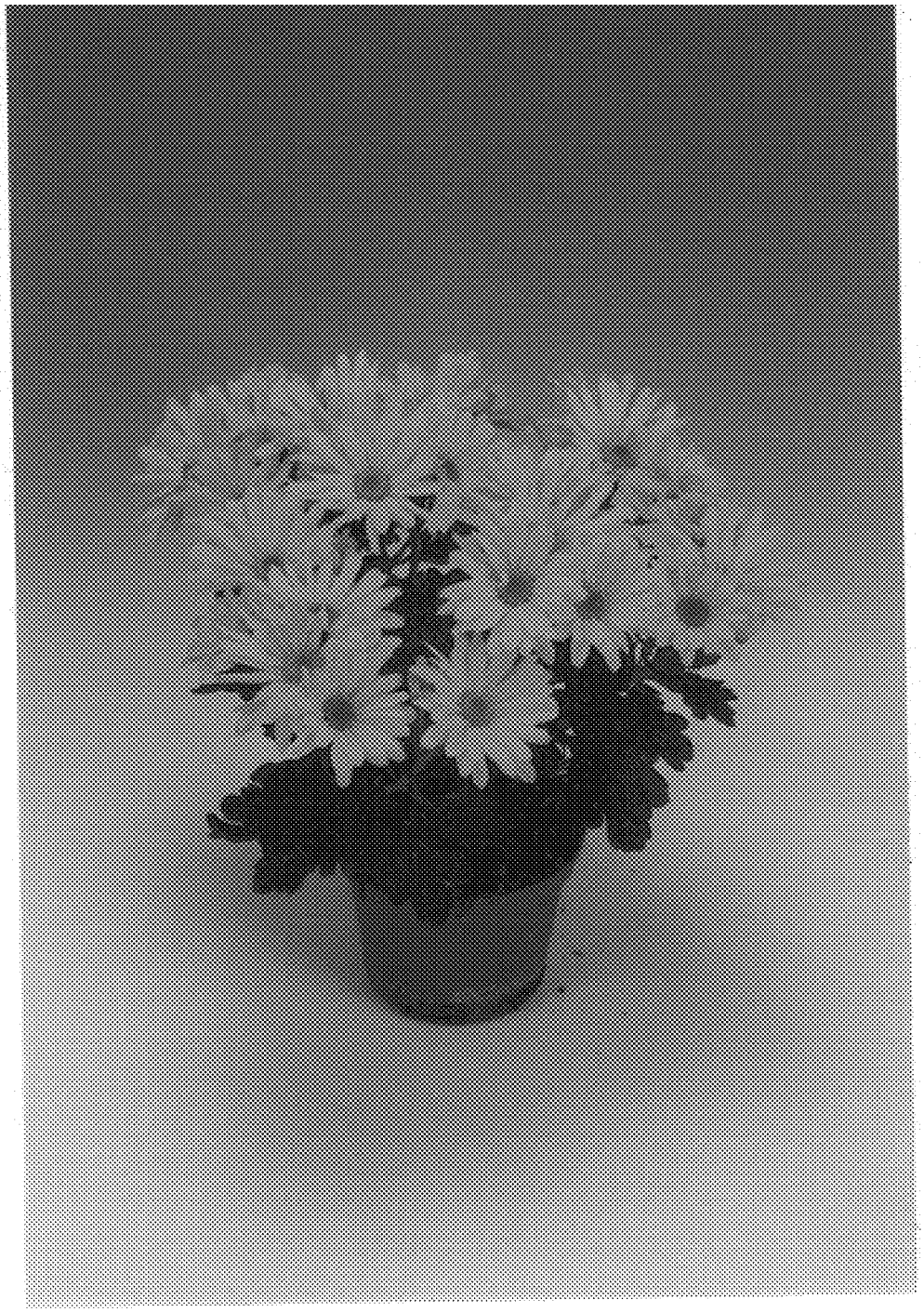
FIG. 1 shows a plant of the cultivar in full bloom.
Figure 2:
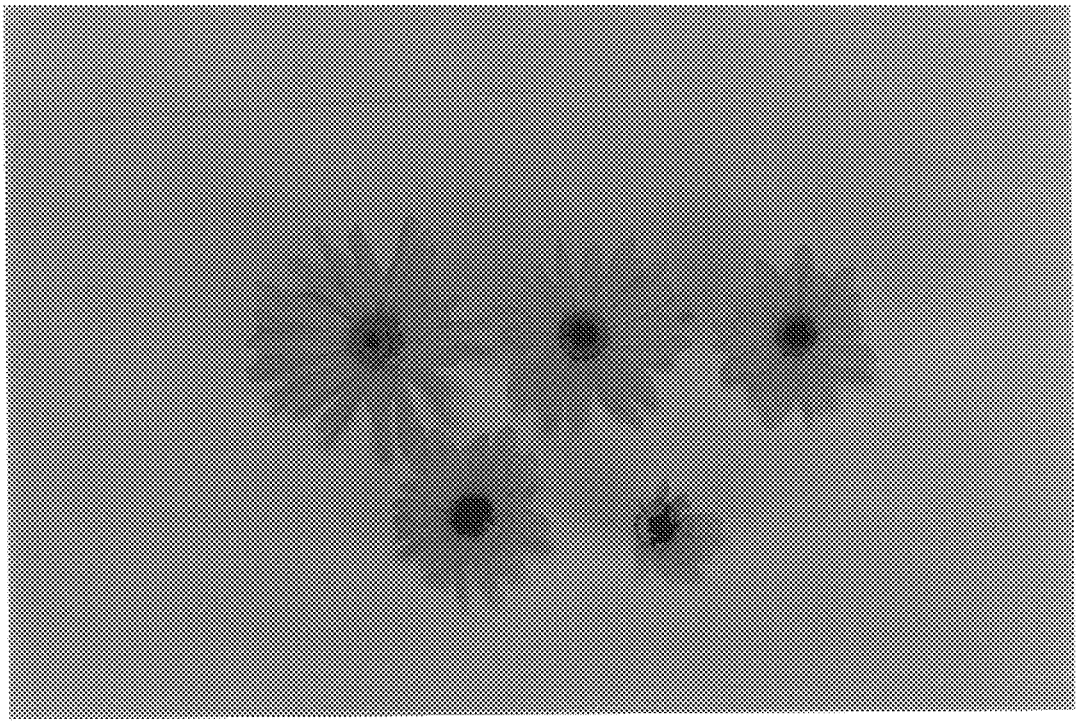
FIG. 2 shows the various stages of bloom of the new cultivar.
Figure 3:
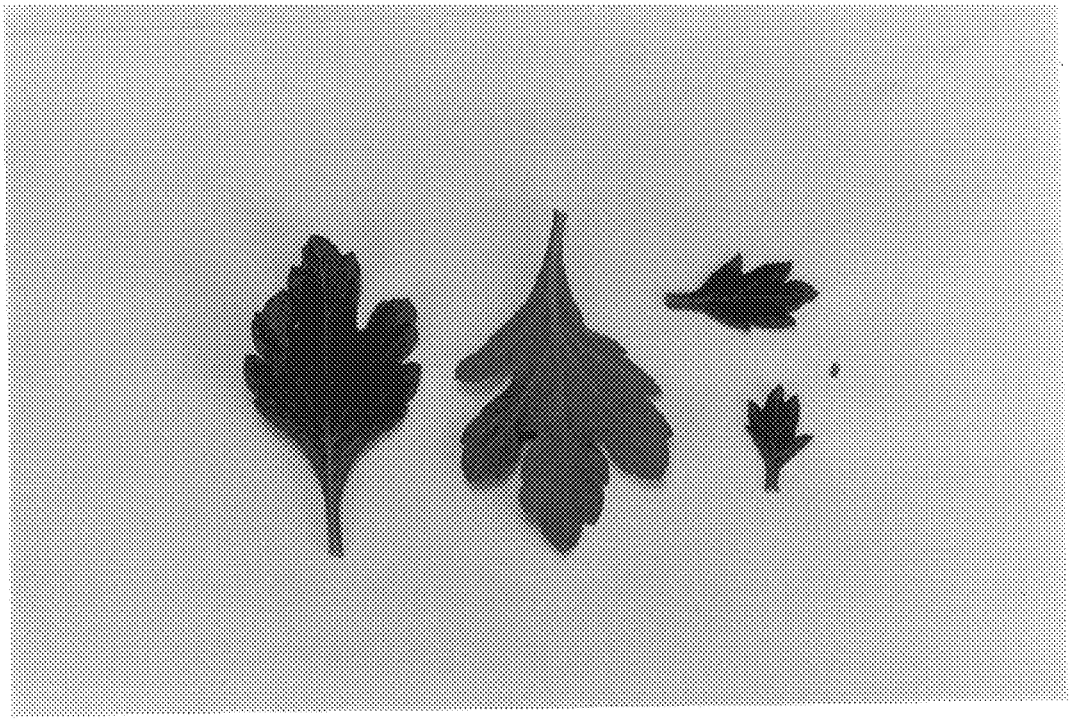
FIG. 3 shows the various stages of foliage and petiole of the new cultivar.

This new variety of chrysanthemum is of the botanical classification *Dendranthema grandiflora*. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 53 days after an average of eight long days. After this long day period to flowering growth retardants were applied 6 times in an average dose of 1.5 gram/liter water. No tests were done on disease or insect resistance or susceptibility. This new variety produces large sized blooms with yellow ray-florets and yellow-green disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'VIRUNGA YELLOW' can be planted without assimilation lightning (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor the most similar existing cultivar in comparison to 'VIRUNGA YELLOW' is VIRUNGA. When VIRUNGA YELLOW and 'VIRUNGA YELLOW' are being compared the following differences and similarities are noticed: The difference of VIRUNGA and 'VIRUNGA' is the ray-floret color for which characteristics 'VIRUNGA YELLOW' has been selected out of VIRUNGA. 'VIRUNGA YELLOW' is yellow, VIRUNGA is yellow-orange. All other characteristics of VIRUNGA and 'VIRUNGA YELLOW' are similar.

From other commercial available varieties known to inventor 'MIRAMAR' (U.S. Plant Pat. No. 7,469) is most similar to 'VIRUNGA YELLOW'. Both varieties have a large yellow daisy flower. Plant habit and shape, foliage form and color are general differences, but also flower color and shape are different. 'virunga yellow' has a lemon yellow flower and the ray-florets are smaller/longer than the ray-florets of 'MIRAMAR'. (3) The disc-floret of 'VIRUNGA YELLOW' is smaller.

The following is a description of the plant and characteristics that distinguish 'VIRUNGA YELLOW' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of CULTIVAR 'VIRUNGA YELLOW' | |
|---|---|
| Bud | |
| Size | Large; Cross-section 1.0 cm height 1.0 cm |
| Outside Color | Green-yellow 1 A |
| Involucral bracts | 2 rows, length 7 mm, width 3 mm |
| Involucral bracts among disc-florets | Not present |
| Involucral bracts color | Yellow-green 146 D |
| Bloom | |
| Type | Daisy |
| Height | Flat |
| Size | Large |
| Fully Expanded | 6.5–7.0 cm. |
| Borne (number of blooms per branch) | Approx. 4 blooms per branch |
| Performance on the plant | 5 weeks |
| Seeds | Not produced |
| Fragrance | Typical chrysanthemum |
| Color | |
| Center of the flower (disc-florets) | Immature yellow-green 144 A<br>Mature yellow-orange 15 C |
| Color of upper surface of the ray-florets | Yellow 3 A |
| Color of the lower surface of the ray-florets | Yellow 4 B |
| Tonality from Distance | A pot mum with large yellow flowers and a green disc |
| Discoloration to color | None |
| Ray florets | |
| Texture | Upper and under side smooth. |
| Number | 27–30 |
| Cross-section | Concave |
| Longitudinal axis of majority | Reflexing |
| Length of corolla tube | Short |
| Ray-floret length | 3.2–3.5 cm. |
| Ray-floret width | 0.8–1.0 cm. |
| Ratio length/width | Medium |
| Shape of tip | Pointed |
| Disc florets | |
| Disc diameter | 1.2–1.4 cm. |
| Distribution of disc florets | Numerous clearly visible at all stages of flowering. |
| Shape | Tubular |
| Color | Yellow-green 144 A |
| Receptacle shape | Conical |
| Reproductive Organs | |
| Stamen (present in disc florets only) | Yellow-green, thick, 4 mm. |
| Number of stamen | Grown together as one |
| Stamen color | Yellow-green 144 C |
| Pollen | Present at mature stage |
| Pollen color | Yellow-orange 12 A |
| Styles (present in both ray and disc florets) | Yellow-green, thin |

TABLE 1-continued

| Botanical Description of CULTIVAR 'VIRUNGA YELLOW' | |
|---|---|
| Style color | Yellow-green 14 C |
| Style Length | 5 mm. |
| Stigmas | Yellow-green |
| Stigma Width | 2 mm. |
| Ovaries | Enclosed in calyx |
| Plant | |
| Form | A pot mum meant for indoor use |
| Growth habit | Spreading |
| Growth rate | Rapid |
| Height | 24–26 cm. |
| Width | 26–28 cm. |
| Stem Color | Yellow-green 146 D |
| Stem Strength | Medium to strong |
| Stem Brittleness | Absent |
| Stem Anthocyanin Coloration | Absent |
| Length of lateral branch | From top to bottom 12–13 cm |
| Lateral branch, attachment | Weak |
| Branching (average number) | Poor with 3 breaks after pinching |
| Peduncle length | 3.5–4.5 cm. |
| Peduncle color | Yellow-green 146 D |
| Flowering Response (photo-periodic controlled crop, not natural season) | 53 days |
| Foliage | |
| Color | Upper side green 137 A<br>under side green 147 B |
| Size | Medium; length 7.0 cm, width 5.0 cm |
| Quantity (number per lateral branch) | 6–8 |
| Shape | Ovate |
| Texture upper side | Glabrous |
| Texture under side | Pubescent |
| Venation arrangement | Palmate |
| Shape of the margin | Serrated |
| Shape of Base of Sinus Between Lateral Lobes | Round |
| Margin of Sinus Between Lateral Lobes | Converging |
| Shape of Base | Rounded (sometimes asymmetric) |
| Apex | Mucronate |

TABLE 2

| Differences with the comparison Varieties | | | |
|---|---|---|---|
| | 'VIRUNGA YELLOW' | 'VIRUNGA' | 'MIRAMAR' |
| Ray-floret color | Yellow 3 A | Yellow-orange 22 A | Yellow 5 A |
| Disc-floret size | 1.2–1.4 cm. | 1.2–1.4 cm. | 1.4–1.7 cm. |

I claim:

1. A new and distinct variety of chrysanthemum plant as described and illustrated.

* * * * *